United States Patent [19]
de Macario et al.

[11] Patent Number: 4,682,890
[45] Date of Patent: Jul. 28, 1987

[54] MICROSAMPLE HOLDER AND CARRIER THEREFOR

[75] Inventors: Everly C. de Macario, Delmar; Robert J. Jovell, Albany; Alberto J. L. Macario, Delmar, all of N.Y.

[73] Assignee: Health Research, Incorporated, Albany, N.Y.

[21] Appl. No.: 739,969

[22] Filed: May 31, 1985

[51] Int. Cl.$^4$ .................. G01N 21/03; C12M 1/18
[52] U.S. Cl. .................. 356/244; 356/246; 435/300; 422/102
[58] Field of Search .............. 250/576; 356/244, 246, 356/300, 319, 440; 435/299, 300, 301; 350/536; 422/102

[56] References Cited

U.S. PATENT DOCUMENTS

| | | | |
|---|---|---|---|
| 3,506,367 | 4/1970 | Ross et al. | 356/246 |
| 3,734,622 | 5/1973 | Adler | 356/246 |
| 3,736,042 | 5/1973 | Markovits et al. | 356/246 |
| 4,197,088 | 4/1980 | Meserol et al. | 356/246 |
| 4,245,052 | 1/1981 | Lund | 356/246 |
| 4,319,841 | 3/1982 | Suovaniemi et al. | 435/301 |
| 4,364,632 | 12/1982 | Pullen | 350/536 |
| 4,387,972 | 6/1983 | Valencia | 356/244 |
| 4,431,307 | 2/1984 | Suovaniemi | 356/246 |
| 4,468,371 | 8/1984 | Chen et al. | 435/300 |

FOREIGN PATENT DOCUMENTS 0135303 3/1985 European Pat. Off. ........... 356/246

OTHER PUBLICATIONS

Fisher Scientific Catalog, 1963, pp. 700 and 701.

*Primary Examiner*—F. L. Evans
*Attorney, Agent, or Firm*—Curtis, Morris & Safford

[57] ABSTRACT

A carrier for use with a microsample holder is described for use in horizontal beam spectrophotometers in place of conventional cuvette supports that normally are used with such spectrophotometers and that carry a plurality of cuvettes and include one or more windows through which the beam passes to samples in the cuvettes. The carrier is formed with a generally rectangular base having a slotted top wall to which a pair of slotted arms is secured at its opposite ends. The arms extend upward from the top wall of the base such that the height of the carrier is substantially equal to the height of the conventional cuvette support, and the slots in the arms and top wall are aligned to provide a guide for a microsample holder. The microsample holder is formed as a plate having a number of retaining elements preferably in the form of a circular perforated area for retaining drops of samples to be analyzed by the spectrophotometer. When the microsample holder is inserted into the slots of the carrier, the retaining elements assume substantially the same position as that portion of the window(s) of the conventional cuvette support which intersect the horizontal beam, whereby no modifications are necessary to the conventional spectrophotometer for use with the carrier and microsample holder.

32 Claims, 9 Drawing Figures

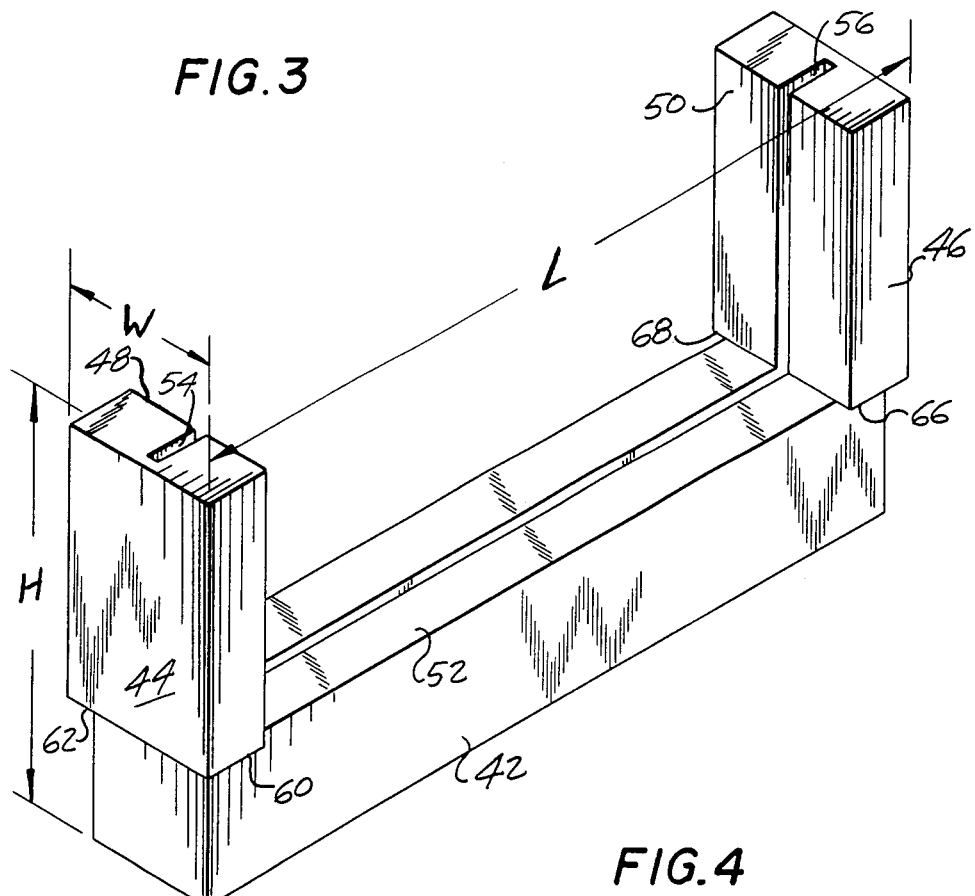
FIG. 3
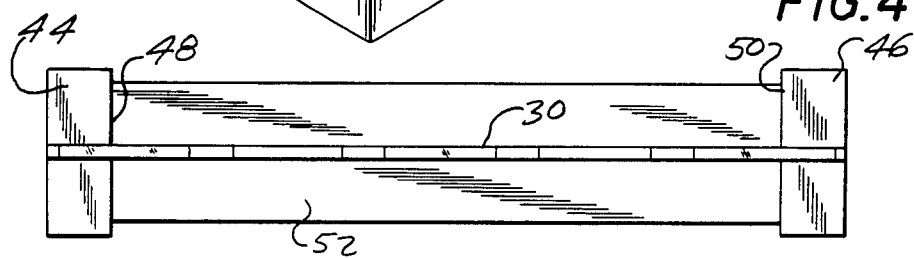
FIG. 4
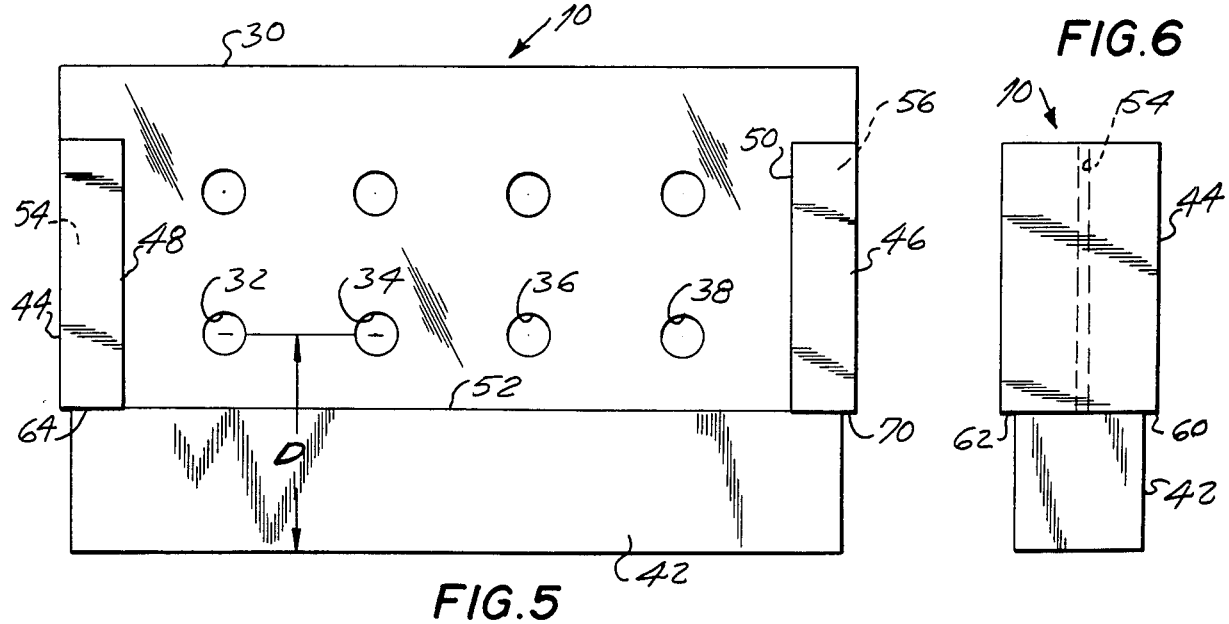
FIG. 5
FIG. 6

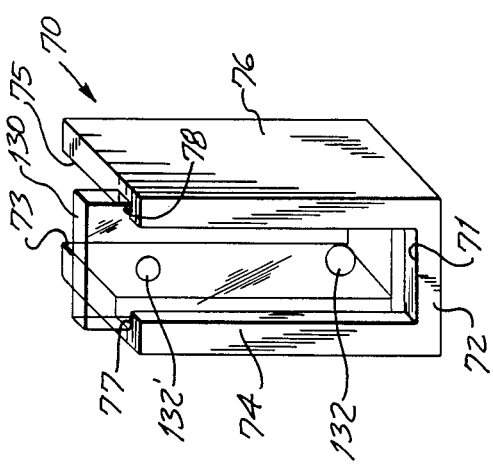

MICROSAMPLE HOLDER AND CARRIER THEREFOR

BACKGROUND OF THE INVENTION

This invention relates to apparatus for use with horizontal beam spectrophotometers and, more particularly, to a carrier adapted to carry a microsample holder, the combination of the carrier and holder being used in place of a conventional cuvette support and cuvettes, whereby the spectrophotometer may be used with the carrier and microsample holder in much the same way as the spectrophotometer heretofore has been used with the conventional cuvette support and cuvettes.

Spectrophotometers have long been used as laboratory tools for analyzing or testing liquid samples of, for example, chemical solutions or mixtures, biologic materials, biochemical materials, biochemical reactions or the like. Typically, two types of spectrophotometers generally are available: the vertical beam spectrophotometer, in which the analyzing light beam is transmitted in the vertical direction to a sample disposed in a horizontal plane; and the horizontal beam spectrophotometer in which the analyzing beam is transmitted in the horizontal direction to impinge a sample disposed in a vertical plane. Of these two types of spectrophotometers, the horizontal beam spectrophotometer is more prevalent.

In using a conventional horizontal beam spectrophotometer, samples of the liquid to be analyzed or tested are contained within individual cuvettes which (shown, for example, in FIG. 9 herein), in turn, are carried by a box-like support that is particularly configured for cooperation with the spectrophotometer. As an example, a conventional support is provided with a holding chamber in which four cuvettes are supported in vertical alignment (shown, for example, in FIG. 1 herein). One or both of the larger faces, or walls, of the support is provided with one or more windows through which the horizontal beam passes to a cuvette supported within the holding chamber thereby exposing that cuvette and its contents to the beam. The window may be of a dimension so as to expose all of the individual cuvettes supported within the supporting chamber or, alternatively, a plurality of individual windows, each aligned with a respective cuvette, may be formed in the larger face(s) of the support. Proper separation of the cuvettes within the supporting chamber is achieved by the provision of internal separating walls that may run the entire height of the support or, alternatively, suitable ribs may be formed on the interior walls of the support to separate the cuvettes and provide sufficient support therefor such that the cuvettes remain in proper vertical alignment notwithstanding the manipulation to which the support may be subjected.

When a horizontal beam spectrophotometer is used with the aforementioned conventional support, each of the cuvettes within that support is exposed, in sequence, to the light beam that is transmitted through the window or windows of that support. Automatic indexing means are provided in some spectrophotometers, whereby the support is indexed to place one cuvette and then the next, in sequence, in the path of the horizontal light beam. In less expensive spectrophotometers, the operator must index the support manually to place successive cuvettes in the path of the light beam. As will be described below, it is one salient feature of the present invention to take advantage of the automatic or manual indexing means by which successive liquid samples in the cuvettes are placed in the path of the horizontal light beam.

While conventional horizontal beam spectrophotometers have been readily accepted, one disadvantage attending the use of cuvettes and the aforementioned conventional cuvette support with that spectrophotometer resides in the fact that each cuvette must contain a relatively large sample, on the order of about 200–2000 $\mu$l. In some instances, the total quantity of sample that is available is relatively small such that it may not be practical to utilize 200 (or 2000) $\mu$l merely for analysis or test purposes. It is, therefore, believed to be desirable to provide apparatus for use with a conventional horizontal beam spectrophotometer which requires the use of far smaller samples, for example, on the order of 5–10 $\mu$l, for analysis or test purposes.

Another disadvantage attending the use of cuvettes and the aforementioned cuvette support is the time-consuming requirement of filling each cuvette and inserting it into the support in preparation for analysis by the spectrophotometer. Typically, the conventional support may contain up to four cuvettes, and each cuvette must be inserted individually into that support. If, for example, eight samples are to be analyzed, as may be common, two separate support-loading operations must be carried out, one before each run through the spectrophotometer. In a typical laboratory analysis procedure, scores of samples are analyzed, and the task of loading the support with groups of four cuvettes becomes significantly time-consuming.

Yet another disadvantage associated with the aforementioned cuvettes and conventional cuvette support is the need to cleanse each cuvette prior to filling it with a liquid sample. Since some cuvettes are relatively expensive, it is not practical to provide an endless supply thereof in a typical laboratory. Hence, after several runs utilizing individual cuvettes, those that had been used previously must be cleansed in preparation for re-use. This cleansing operation, coupled with the aforementioned support-loading operation adds significantly to labor costs and results in inefficiencies.

Although one type of improved microsample holder has been proposed for use with conventional vertical beam spectrophotometers, there has been no comparable suggestion heretofore to employ a similar microsample holder for use with horizontal beam spectrophotometers. Neither has there been any suggestion regarding the use of other supports (carriers) for horizontal beam spectrophotometers. It is believed that the particular structure of conventional box-like cuvette supports, normally used with horizontal beam spectrophotometers, has discouraged attempts to design microsample holders for use therewith. Consequently, there has been no incentive to design new supports for such microsample holders for use in horizontal beam spectrophotometers.

The microsample holder that has been proposed for vertical beam spectrophotometers is constructed as a generally rectangular glass plate having one or more rows of circular areas on the order of about 3 mm in diameter, each circular area being adapted to retain a small liquid sample on the order of a 5 $\mu$l drop. The surface (or surfaces) of the glass plate surrounding the circular areas is coated with a thin layer of hydrophobic material. In one embodiment of the aforementioned microsample holder, one row of, for example, four circular areas are provided in the plate. In other embodiments, two or more rows of circular areas are provided. The use of such microsample holders is described in, for example, Journal of Bacteriology, Volume 149, No. 1, January 1982, "Specific Antisera and Immunological Procedures for Characterization of Methanogenic Bacteria", by Conway de Macario et al., pages 320–328; Journal of Immunological Methods, Volume 59, 1983, "Quantitative Slide Micro-Immunoenzymatic Assay (Micro-SIA) for Antibodies to Particulate and Nonparticulate Antigens", Conway de Macario et al., pages 39–47; and Journal of Immunological Methods, Volume 68, "Slide Immunoenzymatic Assay for Immunoglobulin Isotype (SIA-Ig)", Conway de Macario et al., 1984, pages 311–318.

OBJECTS OF THE INVENTION

Therefore, it is an object of the present invention to provide an improved support or carrier for use with a horizontal beam spectrophotometer, the carrier being adapted to carry a microsample holder yet being capable of retention and manipulation by the spectrophotometer in much the same way as conventional cuvette supports are retained and manipulated by such spectrophotometers.

Another object of this invention is to provide an improved support or carrier for use in a horizontal beam spectrophotometer in place of the conventional cuvette support, which improved support or carrier is adapted to receive and support a microsample holder of the type formed as a plate having a number of elements therein for retaining drops of samples to be analyzed.

A further object of this invention is to provide a carrier for a microsample holder, the carrier being used in a conventional horizontal beam spectrophotometer and being of substantially the same overall dimensions as a conventional cuvette support, the carrier and microsample holder cooperating to dispose samples in substantially the same positions as the usual beam-test portions of the individual cuvettes that are carried by the conventional cuvette support.

An additional object of this invention is to provide a carrier for use with a microsample holder which requires only very small samples of a liquid to be tested or analyzed, which minimizes the preparatory operation by which samples are applied to the microsample holder, which reduces the time needed to load the carrier with samples, and which improves efficiency in testing/analyzing those samples in a horizontal beam spectrophotometer.

Still another object of this invention is to overcome the disadvantages, inefficiencies and defects noted hereinabove with respect to prior art cuvettes and cuvette supports that have been used with horizontal beam spectrophotometers.

Yet a further object of this invention is to provide a carrier that receives a microsample holder, the carrier and holder being insertable into and supported by a conventional cuvette support in place of the cuvette itself.

An additional object of this invention is to provide an improved microsample holder formed as a plate having a number of circular perforated areas for retaining small drops of samples to be analyzed by a spectrophotometer.

Various other objects, advantages and features of the present invention will become readily apparent from the ensuing detailed description, and the novel features will be particularly pointed out in the appended claims.

SUMMARY OF THE INVENTION

In accordance with this invention, apparatus is provided for use in horizontal beam spectrophotometers in place of conventional cuvette supports that normally are used with those spectrophotometers and that support a plurality of cuvettes and are provided with one or more windows through which the beam passes to samples inside the cuvettes. In one embodiment, the apparatus of the present invention is comprised of a carrier formed as a generally rectangular base having a pair of slotted arms secured to and extending outwardly from opposite ends of the base, the height, length and width of the carrier being substantially equal to the height, length and width of the conventional cuvette support. The slots in the arms are aligned to form guide channels to receive microsample holders that are configured as plates having a number of elements that retain a drop or drops of samples to be analyzed by the spectrophotometer. When the plates are inserted into the guide channel formed of the aforementioned slots, the sample-retaining elements assume substantially the same position as the windows of the conventional cuvette support when the carrier is loaded into the spectrophotometer.

In a preferred embodiment, each upstanding arm is rectangular; and the width of each arm, although substantially equal to the width of the conventional cuvette holder, may be equal to or larger than the width of the carrier base. In one embodiment, the end walls of the arms are coplanar with the end walls of the rectangular base. In an alternative embodiment, the distance between the end walls of the arms is greater than the length of the rectangular base; and shoulders are formed between the base and the respective upstanding arms.

The depth of the slots in each arm may be significantly less than the thickness of each arm; and in an alternative embodiment, the slots extend completely through the thickness of the respective arms.

Although a slot in the top wall of the rectangular base is preferred for the purpose of accurately retaining the plate, that slot may be omitted, as described below.

Preferably, the rectangular base and upstanding arms are of one-piece unitary construction.

In another embodiment of this invention, the carrier is inserted into a conventional cuvette support in place of the typical cuvette. In this other embodiment the carrier is formed with a generally square base of dimensions that are substantially the same as the typical cuvette.

BRIEF DESCRIPTION OF THE DRAWINGS

The following detailed description, given by way of example and not intended to limit the present invention solely to the specific embodiments illustrated herein, will best be understood in conjunction with the accompanying drawings in which:

FIG. 3 is a perspective view of another embodiment of the present invention;

FIG. 4 is a top view of the embodiment shown in FIG. 3;

FIG. 5 is a front view of the embodiment shown in FIG. 3;

FIG. 6 is a left-side view of the embodiment shown in FIG. 3;

FIG. 7 is a perspective view of one embodiment of a carrier insertable into a conventional cuvette support in place of the typical cuvette;

FIG. 8 is a perspective view of yet another embodiment of a carrier that may be inserted into a cuvette support; and FIG. 9 is a perspective view of a typical cuvette.

DETAILED DESCRIPTION OF CERTAIN PREFERRED EMBODIMENTS

Figure 1:
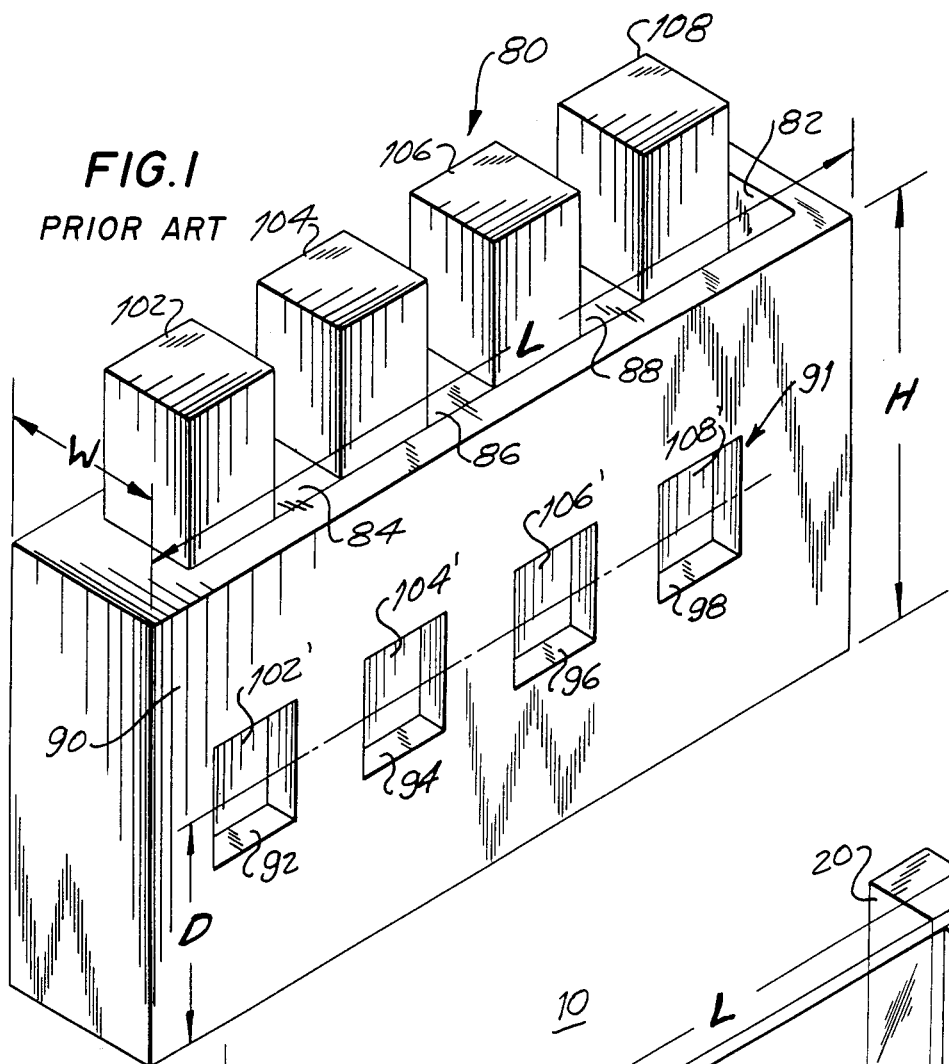
FIG. 1 is a perspective view of a conventional cuvette support normally used with a horizontal beam spectrophotometer.

The advantages achieved by the present invention will best be appreciated by comparison with a conventional cuvette support and conventional cuvettes. Accordingly, reference is made to FIG. 1 in which a conventional cuvette support 80 is illustrated. This cuvette support is a rectangular box-like structure having a supporting chamber 82 adapted to contain a number of cuvettes. Typically, four cuvettes 102, 104, 106 and 108, each containing a sample of approximately 200–2000 µl, are contained within supporting chamber 82.

To assure proper alignment of the cuvettes within the supporting chamber, the supporting chamber may be subdivided into four separate compartments by, for example, separators 84, 86 and 88, respectively. These separators may be formed as ribs extending upwardly from the base of support 80, downwardly from the top wall thereof and inwardly from the front and rear walls. Alternatively, the separators may comprise interior walls that extend from the top to the bottom of chamber 82. Front wall 90 of support 80 is provided with a window 91 through which the horizontal beam of the spectrophotometer passes to the samples within cuvettes 102, 104, 106 and 108. In one version, the front wall of support 80 is provided with a single rectangular window. In another version, such as the one illustrated in FIG. 1, window 91 is comprised of individual windows 92, 94, 96 and 98 which expose beam test portions 102', 104', 106' and 108', respectively, of the cuvettes.

In one type of conventional horizontal beam spectrophotometer, the analyzing light beam passes through the cuvette to a target detector disposed on and separate from the opposite side of support 80. The support thus may be provided with a window similar to window 91 (or similar to individual windows 92, 94, 96 and 98) in its rear wall (not shown). It is appreciated that, with this type of spectrophotometer, the light beam may be subjected to refraction or interference due to the glass walls of the cuvette through which that beam must pass. In another type of horizontal beam spectrophotometer, the so-called reflecting type, the light beam passes through the beam test portion of the cuvette and is reflected back through that beam test portion to a suitable detector located opposite front wall 90 of support 80. Here too, the beam is subjected to refraction or interference due to the glass walls of the cuvette through which that beam is transmitted and reflected.

When used with a conventional horizontal beam spectrophotometer, support 80, containing cuvettes 102, 104, 106 and 108, is loaded into a suitable support-receptacle of the spectrophotometer (not shown), and the support then is indexed, either automatically or manually, to position beam test portions 102', 104', 106' and 108' successively in the path of the analyzing beam. An attempt has been made to form the support-receptacle of the spectrophotometer with standardized dimensions, and a typical though not necessarily standard support-receptacle is found in the Gilford Model 250 spectrophotometer which cooperates with a support having a length L of 75 mm, a height H of 42 mm and a width W of 19 mm. These dimensions are illustrated in FIG. 1. The analyzing beam of the spectrophotometer passes through the individual beam test portions 102', 104', 106' and 108' at a distance D above the base of the conventional support 80.

Typically, after four samples contained within cuvettes 102, 104, 106 and 108 have been analyzed, these samples are returned to the respective sources from which they were obtained; and the cuvettes then are cleaned and prepared to receive samples of other liquids. As mentioned above, this operation of cleansing each cuvette and then filling that cuvette with a fresh sample is time-consuming. Also, since each cuvette holds approximately 200–2000 µl of the sample, a relatively large amount of liquid must be sampled for spectrophotometer analysis. In some instances, this large requirement may be difficult to spare or may be impractical to provide.

Figure 2:
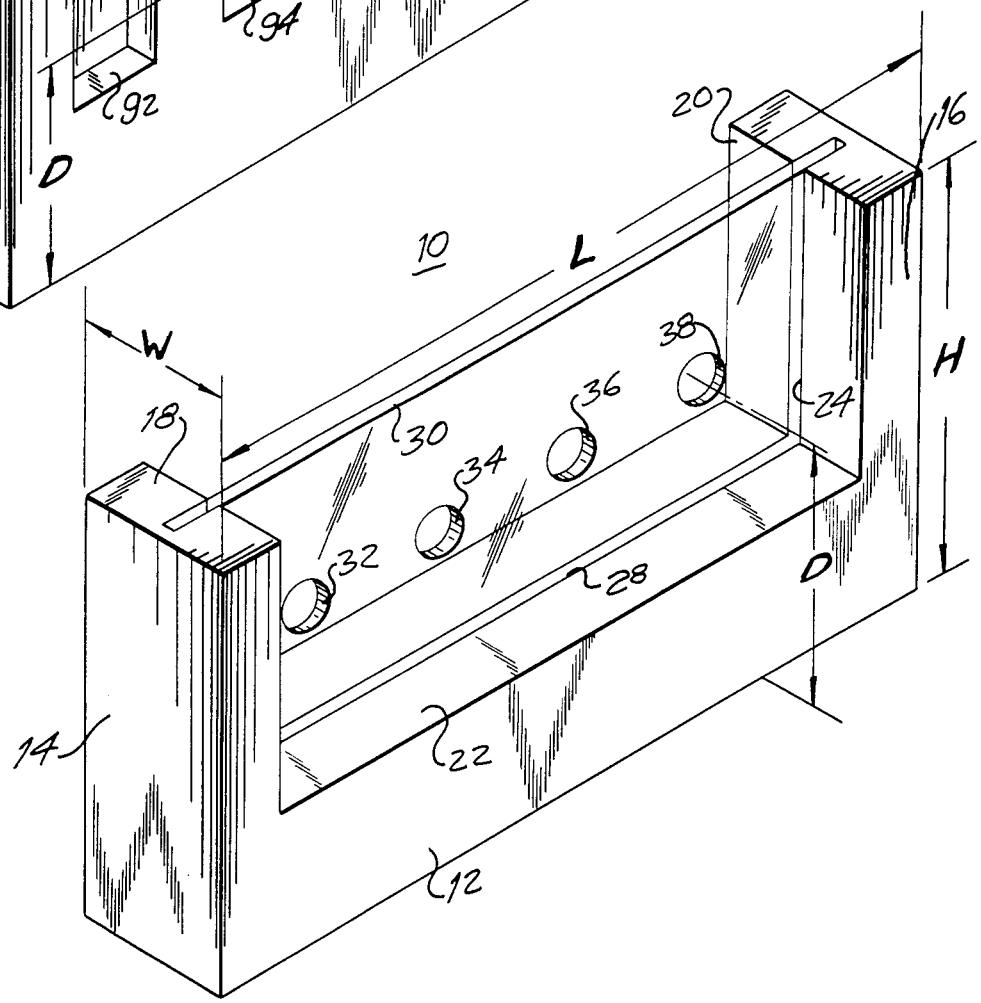
FIG. 2 is a perspective view of one embodiment of the present invention.

One example of a carrier in accordance with the present invention is illustrated in FIG. 2. Here, carrier 10 is comprised of a generally rectangular base 12 having a pair of arms 14 and 16 extending upwardly from a top wall 22 of the base. Preferably, base 12 and arms 14, 16 are formed of one-piece unitary construction. The materials from which carrier 10 is constructed may be identical to the materials normally used to construct conventional cuvette support 80, such as metal, plastic or the like. The length L of carrier 10, extending from the outer wall or surface of arm 14 to the outer wall or surface of arm 16, is equal to the length L of support 80. Similarly, the height H of carrier 10 from the top wall, or surface, of an arm to the bottom surface of base 12 may be equal to the height H of the conventional cuvette support. Finally, the width W of each arm of carrier 10 is equal to the width W of the conventional cuvette support. Thus, it is seen that the external dimensions of carrier 10 of the present invention are substantially identical to the external dimensions of the conventional cuvette support 80 shown in FIG. 1.

Carrier 10 is adapted to carry a microsample holder 30 that is formed as a generally rectangular plate having, for example, dimensions on the order of 25×70×1 mm. An example of the microsample holder plate 30 is illustrated in FIG. 2, and this plate is suitably positioned within guide slots (only guide slot 24 is shown) formed on inner walls 18 and 20 of arms 14 and 16, respectively, as well as a guide slot 28 formed in top wall 22 of base 12. Preferably, but not necessarily, the guide slots are generally centrally located in the respective inner walls of arms 14 and 16 and also in top wall 22. These guide slots may be offset from center, if desired. In the embodiment illustrated in FIG. 2, the guide slots extend a depth significantly less than the thickness of each arm. It is appreciated that the purpose of the guide slots is to position and properly align plate 30 which is easily inserted from above carrier 10 and removed therefrom. As will be explained below, guide slot 28 may be omitted from top wall 22, if desired. Alternatively, the length of plate 30 may be equal to the length of the carrier (e.g. 75 mm), or longer, whereby guide slot 24, as well as the guide slot (not shown) disposed in inner wall 18 of arm 14, may extend completely through the thickness of the respective arm.

Plate 30 is formed with a set of retaining elements, such as a row of four retaining elements 32, 34, 36 and 38. When plate 30 is fully inserted into the guide slots of carrier 10, the retaining elements are located a distance D above the bottom surface of base 12, thus aligning the retaining elements with the horizontal analyzing beam that normally passes through beam test portions 102', 104', 106' and 108' of the conventional cuvette support 80 shown in FIG. 1. Retaining elements 32, 34, 36 and 38 are of circular shape having diameters on the order of about 3 mm, each retaining element being capable of retaining a 5–10 $\mu l$ sample of liquid to be analyzed. The surfaces of plate 30 other than the circular areas may be coated with a thin layer of hydrophobic material to assure retention of the liquid samples within the circular areas. Each circular sample-retaining area may be formed as a relatively thin flat dish or, preferably, may be merely a circular hole such that plate 30 is formed as a perforated web. This circular hole, of the aforementioned diameter, permits the surface tension of the liquid sample to retain that sample stably within the confines of the hole. Plate 30 may be handled without dislodging the liquid sample retained in the circular hole. In the case of a thin flat dish, the material of the dish must be permeable to light of many wave lengths for use with transmission-type spectrophotometers so as to allow the analyzing beam to pass through the sample as well as the retaining dish to the spectrophotometer detector. Although the remainder of plate 30 need not be light transmissive, it is, nevertheless, advantageous to its construction to construct the plate of transparent material, such as glass, plastic, quartz or the like. It is appreciated that, since the analyzing beam need pass through only a single layer of transparent material, (i. e. the thin flat dish), only minimal refraction or interference of the beam results. This compares favorably with more substantial refraction or interference that is present when the conventional cuvette (FIG. 1) is used, i. e. refraction of the analyzing beam due to its passage through the front and rear glass walls of the cuvette.

If carrier 10 and microsample holder 30 are used with a reflective-type spectrophotometer, it is appreciated that circular thin flat dishes 32, 34, 36 and 38 may be formed of appropriate light-reflecting material.

Although holder 30 is illustrated with a single row of retaining elements 32, 34, 36 and 38, it is appreciated that two or more rows of retaining elements may be provided, if desired, such as shown in FIG. 5. For example, if two rows of four 34 retaining elements each are formed in holder 30, samples may be applied to each retaining element and then, after holder 30 is inserted into carrier 10 and the first row of samples is analyzed, holder 30 then may be removed from the carrier, inverted and then re-inserted into the carrier to permit the next row of samples to be analyzed. It is appreciated that this simple operation of removal, inversion and re-insertion of the holder into carrier 10 is far simpler and faster than the removal of cuvettes from cuvette support 80, the cleansing of those cuvettes and then the re-insertion of the cleansed cuvettes into the cuvette support.

Since the overall height, length and width of carrier 10 are identical (or substantially identical) to the height, length and width of the conventional cuvette support shown in FIG. 1, it is recognized that carrier 10 is readily usable with the normal support-receptacle and automatic or manual indexing mechanism of conventional horizontal beam spectrophotometers. Thus, retaining elements 32, 34, 36 and 38 are aligned with the analyzing beam that normally passes through windows 92, 94, 96 and 98 of conventional cuvette support 80. That is, the small 5-10 $\mu l$ samples carried by microsample holder 30 are positioned as suitable targets for the analyzing beam in place of the much larger targets (or beam test portions) 102', 104', 106' and 108' of the conventional arrangement shown in FIG. 1. It is seen that the analyzing beam thus passes through the center of each sample retained by retaining elements 32, 34, 36 and 38. Of course, the beam passes through only one sample at a time, and as carrier 10 is indexed, successive samples are exposed to the beam.

Turning now to the alternative embodiment shown in FIGS. 3–6, it is seen that carrier 10 is comprised of a generally rectangular base 42 having a top wall 52 from which a pair of upstanding arms 44 and 46 extend. In this embodiment, as in the previously described embodiment, arms 44 and 46 are provided with inner walls 48 and 50 in which slots 54 and 56, respectively, are disposed. As before, these slots are positioned preferably centrally of the width W of the upstanding arms and are adapted to receive and align holder 30 therein. Holder 30 is here illustrated as including two rows of retaining elements, each retaining element preferably being formed as a 3 mm circular hole. The advantage of providing two rows of retaining elements has been described above. In the embodiment shown in FIGS. 3–6, top wall 52 is provided with a slot; but it is fully appreciated that, if desired, this slot may be omitted.

In the embodiment presently described, the distance between the top surface of arm 44 (or arm 46) and the bottom surface of base 42 is equal to the height H of the conventional cuvette support 80 (FIG. 1), and the length L between the outer walls of arms 44 and 46 is equal to the length L of the conventional cuvette support. The width W of each arm likewise is equal to the width of the conventional cuvette support shown in FIG. 1.

As best shown in FIGS. 3, 4 and 6, the width W of each arm is greater than the width of base 42, thus resulting in shoulders 60, 62 between base 42 and arm 44, and shoulders 66, 68 between the base and arm 46. Also, it is seen that the length L between the outer walls of arms 44 and 46 is greater than the length of base 42, thus resulting in a further shoulder 64 between arm 44 and base 42 and another shoulder 70 between the base and arm 46, as best shown in FIG. 5.

In the embodiment shown in FIG. 2, the height of microsample holder 30 is substantially equal to the height of arm 14 (16) extending above wall 22 of base 12. In the embodiment shown in FIGS. 4 and 5, the height of holder 30 is seen to be greater than the height of arm 44 (46). Nevertheless, in both embodiments, it is appreciated that carrier 10 is adapted to receive and hold microsample holder 30 such that retaining elements 32, 34, 36 and 38 are positioned to be in alignment with the horizontal beam of the spectrophotometer. That is, these retaining elements are in substantially the same positions as windows 92, 94, 96 and 98, or test portions 102', 104', 106' and 108', which form the intended targets of the analyzing beam.

From the foregoing description of two embodiments of the present invention, it is seen that arms 14, 16 or arms 44, 46 are provided with slots which extend substantially the length of the arms. This facilitates insertion and removal of microsample holder 30. The overall length of microsample holder 30 may, in large part, determine the depth of these slots. Further, it is seen that base 12 (42) may be provided with a slot 28 which is aligned with and meets the slot of the upstanding arms (FIG. 2). Or the slot may be omitted from the base (FIGS. 3–6). Additionally, it is seen that each arm 14, 16 (44, 46) is rectangular so as to closely resemble the shape and configuration of the conventional cuvette support shown in FIG. 1. Moreover, to enable the carrier of the present invention to be received by the same conventional support-receptacle normally provided in typical horizontal beam spectrophotometers, the end walls of base 12 or base 42 are seen to be planar. Of course, in both embodiments described herein, when carrier 10 is loaded into a conventional horizontal beam spectrophotometer, retaining elements 32, 34, 36 and 38 assume the same position as beam test portions 102', 104', 106' and 108' of the cuvettes normally carried by conventional cuvette support 80. Thus, when the carrier of the present invention is used with that conventional spectrophotometer, the retaining elements assume substantially the same position as the windows of the conventional cuvette support and, therefore, the horizontal analyzing beam of the spectrophotometer impinges the retaining elements.

Another example of a carrier in accordance with a further embodiment of the present invention is illustrated in FIG. 7. Carrier 70 is comprised of a generally square base 72, similar to the square base of a typical cuvette, such as cuvette 102 shown more clearly in FIG. 9. A pair of arms 74 and 76 extend upwardly from a top wall 71 of base 72. Preferably, base 72 and arms 74, 76 are formed of one-piece unitary construction of materials that may be used in the construction of aforementioned carrier 10, such as metal, plastic, or the like. The overall dimensions of carrier 70, i. e. its height and base, are substantially equal to the overall dimensions of the typical cuvette shown in FIG. 9. Hence, carrier 70 is readily adapted to be contained in conventional cuvette support 80 (FIG. 1).

Carrier 70 is adapted to carry a microsample holder 130 that is formed as a generally rectangular plate, this plate being formed of the same materials as aforementioned plate 30 and, preferably, having only a single column of retaining elements to retain 5–10 $\mu$l samples of liquid to be analyzed. Plate 30 may be provided with only a single retaining element 132 (analogous to a single row of retaining elements mentioned above in conjunction with FIG. 2), or with two retaining elements 132 and 132' (analogous to the two rows of retaining elements mentioned above in conjunction with FIG. 5). Each retaining element preferably is formed as a circular hole of about 3 mm diameter. Microsample holder 130 is suitably positioned within guide slots 77 and 78 formed on inner walls 73 and 75 of arms 74 and 76, respectively, these guide slots being shown offset from the center of carrier 70 but may be centrally located in arms 74, 76, if desired. A guide slot also may be provided in top wall 71 of base 72, but such an additional guide slot is not illustrated herein. As before, the purpose of the guide slots is to position and properly align plate 130 which is inserted from above carrier 70 and removed therefrom.

It will be recognized that retaining element 132 serves to retain a sample of liquid in position corresponding to the beam test portion (such as beam test portion 102' of FIG. 1) of the typical cuvette 102 when that cuvette is contained in conventional support 80. Hence, when carrier 70 and plate 130 are inserted into that conventional support, the liquid sample retained by retaining element 132 is aligned with window 92, for example, and is a properly positioned target for the analyzing beam of the spectrophotometer. Of course, the retained sample is on the order of 5–10 $\mu$l as opposed to the much larger sample of 200–2000 $\mu$l normally used in typical cuvettes. If plate 130 is provided with additional retaining element 132', a sample retained therein may be positioned as a beam target merely by removing the plate from carrier 70, inverting it, and then reinserting it into the column.

FIG. 7 illustrates a so-called single plate carrier 70 in which a single plate microsample holder 130 is inserted. A double plate carrier 70' is illustrated in FIG. 8 (wherein like reference numerals are used) and this double plate carrier differs from the aforedescribed single plate carrier in that another pair of guide slots 79, 81 is provided in arms 74, 76, respectively, to receive and position another microsample holder plate 134. Nevertheless, the overall dimensions of carrier 70' are the same as those of carrier 70 which, as mentioned above, are substantially the same as those of typical cuvette 102.

Guide slots 77, 78 and 79, 81 are spaced from each other such that plates 130 and 134 are separated by a relatively small distance. Plate 134 is substantially identical to plate 130 and is provided with a retaining element 136 aligned with retaining element 132. Plates 130 and 134 may be provided with additional, aligned retaining elements, not shown, similar to additional retaining element 132' (FIG. 7). The small separation between plates 130 and 134 enables the liquid sample placed on retaining element 132 (or on retaining element 136) or on retaining element 132', to form a liquid bridge suspended between the retaining elements of the adjacent plates. This liquid sample may be on the order of about 10 $\mu$l.

Thus, it is seen that carrier 70 of FIG. 7 and carrier 70' of FIG. 8 are of substantially the same overall dimensions as the typical cuvette (shown in FIG. 9) and may be used in place of that cuvette in the conventional carrier 80. Of course, carriers 70, 70' may be used with vertical beam spectrophotometers and in other applications in which the typical cuvette heretofore has been used. Advantageously, the liquid sample retained by the microsample holder(s) used with carrier 70 (or 70') may be on the order of 5–10 $\mu$l, as compared to the 200–2000 $\mu$l sample heretofore used with the typical cuvette. Also, the procedure by which a liquid sample is replaced in carrier 70 (70') is far simpler and quicker than the procedure used to replace the sample contained in a typical cuvette. It merely is necessary to substitute a new plate 130 (or new plates 130, 134) in carrier 70 (70'); rather than empty, clean and re-fill the cuvette.

The circular retaining elements of holders 30, 130 and 134 are capable of permitting chemical, biochemical and biological reactions to be performed with the liquid samples retained thereon. For example, reagents or biologicals may be pre-anchored to the circular surfaces of the thin, flat dishes or to the inner surfaces of the circular perforated webs which comprise the retaining elements. Then, when liquid samples are applied to these retaining elements, the samples come into contact with the pre-anchored reagents or biologicals, resulting in onboard, uninterrupted reactions to commence and progress when the samples are introduced into the spectrophotometer for analysis, as discussed above. Consequently, the need to transfer reactants from a reactant vessel to a cuvette, as heretofore required on a sample-by-sample basis, is obviated. Rather, holders 30, 130 and 134 may be prepared with reactants in advance, to await the application of small sample drops to the thus-prepared retaining elements.

While the present invention has been particularly shown and described with reference to preferred embodiments, it will be readily appreciated by those of ordinary skill in the art that various changes and modifications may be made without departing from the spirit and scope of the present invention. For example, holder 30 (as well as holders 130 and 134) may be provided with two, three or more rows of retaining elements, and each row may be formed of one or more retaining elements. It merely is necessary, for the embodiment of FIGS. 2-6, that the carrier in which holder 30 is inserted be of substantially the same overall dimensions as the conventional cuvette support so as to simulate that conventional cuvette support when loaded into a typical horizontal beam spectrophotometer; and for the embodiment of FIGS. 7 and 8, that the carrier for holder 130 (134) be of substantially the same overall dimensions as the typical cuvette so as to simulate that cuvette when loaded into a conventional cuvette support. When so loaded, the retaining elements of the carrier(s) assume the same positions within the spectrophotometer as the usual windows which normally are provided in the conventional cuvette support.

It is, therefore, intended that the appended claims be interpreted as including not only the embodiments specifically disclosed herein but other equivalent arrangements thereto.

What is claimed is:

1. Apparatus for use in a horizontal beam spectrophotometer in place of a conventional cuvette support that normally is used with said spectrophotometer and that carries a plurality of cuvettes and includes one or more windows through which the beam passes to samples in said cuvetes; said apparatus comprising a carrier formed as a generally rectangular base having opposite ends, a bottom surface, a top wall and a slot in the top wall thereof, a pair of arms secured to said opposite ends of said base and extending upwardly from said top wall such that the height of said carrier from the top of either arm to the bottom surface of said base is substantially equal to the height of the conventional cuvette support, each arm having an inner wall that faces the inner wall of the other arm and in which is disposed a slot aligned with and meeting the slot in the top of said base and extending substantially the length of said arm; and a microsample holder formed as a plate having a number of retaining elements for retaining drops of samples to be analyzed by said spectrophotometer, said plate being insertable in the slots of said carrier to position the plate on said base such that when said carrier is loaded into said spectrophotometer the retaining elements assume substantially the same position as the windows of said conventional cuvette holder.

2. The apparatus of claim 1 wherein each of said upstanding arms is rectangular and is provided with an outer wall, the distance from the outer wall of one arm to the outer wall of the other arm being substantially equal to the length of the conventional cuvette support.

3. The apparatus of claim 2 wherein the width of each arm is substantially equal to the width of the conventional cuvette support.

4. The apparatus of claim 3 wherein the width of the base is substantially equal to the width of each arm.

5. The apparatus of claim 3 wherein the width of the base is less than the width of each arm.

6. The apparatus of claim 5 wherein the length of the base is less than the distance from the outer wall of one arm to the outer wall of the other arm.

7. The apparatus of claim 3 wherein the length of the base is substantially equal to the distance from the outer wall of one arm to the outer wall of the other arm.

8. The apparatus of claim 2 wherein said base is provided with planar end walls.

9. The apparatus of claim 2 wherein said base and arms are of one-piece, unitary construction.

10. The apparatus of claim 1 wherein the slots in each arm extend completely through the thickness of said each arm.

11. For use in a spectrophotometer, and particularly a horizontal beam spectrophotometer, a carrier for a microsample holder of the type formed as a plate having a number of retaining elements for retaining drops of samples to be analyzed by said spectrophotometer, said carrier comprising a base having opposite ends; a pair of upstanding arms respectively secured to said opposite ends of said base, said arms having inner walls that face each other, a guide slot disposed in the inner wall of each arm, said guide slot running substantially the entire length of the arm in which it is disposed and being generally centrally located in said inner wall; the guide slots receiving said holder plate and positioning said plate on said base such that when said carrier is loaded into said spectrophotometer, the retaining elements assume the same position as the usual beam-test portions of the individual cuvettes that normally are carried by a conventional cuvette support and that are exposed to the spectrophotometer beam through windows of said conventional cuvette support.

12. The carrier of claim 11 wherein said base and arms are of one-piece unitary construction.

13. The carrier of claim 11 wherein the length, height and width thereof are substantially equal to the length, height and width of said conventional cuvette support.

14. Apparatus for use in a conventional cuvette support in place of a conventional cuvette that normally is used with said support, said apparatus comprising a carrier formed as a base having opposite ends and having substantially the same configuration as the cross-section of said conventional cuvette; a pair of upwardly extending arms secured to said opposite ends of said base, each arm having an inner wall that fasces the inner wall of the other arm and in which is disposed at least one slot extending substantially the length of said arm; and at least one microsample holder formed as a plate having a retaining element for retaining a drop of liquid sample, said plate being insertable in the slots of said carrier to position the plate on said base.

15. The apparatus of claim 14 wherein said base is generally square.

16. The apparatus of claim 15 wherein the distance from the bottom of said base to the top of said plate when the latter is inserted in the slots of said carrier is substantially equal to the height of said cuvette.

17. The apparatus of claim 14 wherein said base and arms are of one-piece, unitary construction.

18. The apparatus of claim 14 wherein each arm is provided with a pair of spaced apart slots; and said microsample holder is formed as a pair of plates, each insertable in a respective slot in each arm, and each having a retaining element for retaining a drop of liquid sample that is suspended between the retaining elements of said plates.

19. Apparatus for retaining a number of liquid samples comprising a base having opposite sides; a pair of upwardly extending arms secured to said opposite sides of said base, each arm having an inner wall that faces the inner wall of the other arm and in which is disposed a slot extending substantially the length of said arm; and a microsample holder formed as a plate having a number of retaining elements for retaining respective drops of liquid sample, said plate being insertable in the slots of said carrier to position the plate on said base.

20. The apparatus of claim 19 wherein said base is substantially rectangular, and said microsample holder has at least one row of retaining elements.

21. The apparatus of claim 19 wherein said base is generally square and said microsample holder has one retaining element.

22. The apparatus of claim 19 wherein said base is generally square, each said arm is provided with two slots, and two microsample holders are insertable in respective pairs of slots, each microsample holder having a retaining element for suspending a liquid bridge between the retaining elements of said microsample holders.

23. A microsample holder for retaining at least one drop of liquid sample, comprising a thin, flat plate; and at least one circular opening in said plate having a diameter on the order of 3 mm for retaining said liquid sample therein.

24. The holder of claim 23 wherein said microsample holder is formed of material selected from the group consisting of glass, plastic and quartz.

25. The holder of claim 23 wherein a column of substantially identical circular openings is provided in said microsample holder.

26. The holder of claim 25 wherein said column consists of two substantially identical circular openings.

27. The holder of claim 23 wherein a row of substantially identical circular openings is provided in said microsample holder.

28. The holder of claim 27 wherein two rows of substantially identical circular openings are provided in said microsample holder.

29. The holder of claim 28 wherein each row consists of four substantially identical circular openings.

30. The holder of claim 23 wherein said circular opening retains a drop of liquid on 5–10 $\mu$l.

31. The holder of claim 23, further including a second thin, flat plate substantially identical to the first-mentioned plate and spaced therefrom, said second plate having at least one circular opening aligned with the circular opening in said first plate, the aligned openings supporting a liquid bridge suspended therebetween.

32. The microsample holder of claim 23 further including a reagent on the inner surface of said at least one circular opening for reacting with a drop of liquid sample applied to said at least one opening.

* * * * *

UNITED STATES PATENT AND TRADEMARK OFFICE
CERTIFICATE OF CORRECTION

PATENT NO. : 4,682,890
DATED : July 28, 1987
INVENTOR(S) : Everly Conway de Macario et al.

It is certified that error appears in the above-identified patent and that said Letters Patent are hereby corrected as shown below:

Correct the last name of the first-named inventor to read as follows: --Conway de Macario--.

Claim 1, column 11, line 49, after "top" insert --wall--.

Claim 14, column 12, line 49, correct the spelling of "faces".

Signed and Sealed this

Seventeenth Day of November, 1987

Attest:

DONALD J. QUIGG

Attesting Officer

Commissioner of Patents and Trademarks